United States Patent
Zhang et al.

(10) Patent No.: US 8,888,997 B2
(45) Date of Patent: Nov. 18, 2014

(54) CENTRALIZED SUPPLY SYSTEM FOR ELECTROLYZED OXIDIZING WATER AND INTELLIGENT CONTROL METHOD THEREOF

(75) Inventors: Dunjie Zhang, Beijing (CN); Xiangbing Kong, Beijing (CN)

(73) Assignee: Global Resource Envi-Tech Co., Ltd., Beijing (CN)

(*) Notice: Subject to any disclaimer, the term of this patent is extended or adjusted under 35 U.S.C. 154(b) by 481 days.

(21) Appl. No.: 13/239,904

(22) Filed: Sep. 22, 2011

(65) Prior Publication Data

US 2012/0067795 A1 Mar. 22, 2012

(30) Foreign Application Priority Data

Mar. 26, 2009 (CN) .......................... 2009 1 0119759

(51) Int. Cl.
*C02F 1/30* (2006.01)
(Continued)

(52) U.S. Cl.
CPC ................ *C02F 1/467* (2013.01); *A61L 2/035* (2013.01); *A61L 2202/14* (2013.01);
(Continued)

(58) Field of Classification Search
CPC .............. C02F 1/30; C02F 1/46; C02F 1/467; C02F 1/66; C02F 1/72; C02F 1/461; C02F 1/46104; C02F 2201/461; C02F 2201/4612; C02F 2201/46105; C02F 2201/4611; C02F 2201/46146; C02F 2201/4615; C02F 2201/4618; C25B 1/00; C25B 1/04; C25B 5/00
USPC ................ 210/86, 104, 143, 138, 198.1, 243, 210/257.1, 263, 663, 748.01, 259, 743, 210/758; 204/157.1, 555, 556, 228.1, 204/228.2, 228.3, 229.2; 205/334, 464; 426/66; 423/580.1
See application file for complete search history.

(56) References Cited

U.S. PATENT DOCUMENTS 2,794,776 A * 6/1957 Briggs .......................... 210/669
5,624,535 A * 4/1997 Tsuchikawa et al. ...... 204/228.2
(Continued)

FOREIGN PATENT DOCUMENTS

CN 101178589 A 5/2008
CN 201156196 Y 11/2008
(Continued)

OTHER PUBLICATIONS

Derwent Abstract for JP 2003-80252, Mar. 2003.*
(Continued)

*Primary Examiner* — Joseph Drodge
(74) *Attorney, Agent, or Firm* — Staas & Halsey LLP

(57) ABSTRACT

A centralized supply system for electrolyzed oxidizing water comprises a water softener (1), several parallel electrolyzed oxidizing water generators (2) connected, liquid storage tanks (3, 4) and delivery pumps (5, 6). A central controller (10) implements independent control over the several parallel electrolyzed oxidizing water generators (2). Liquid level sensors (9) are mounted in the liquid storage tanks (3, 4) and are connected with the central controller (10) via data collection cables (12). With the detection, determination and calculation for the liquid level signal in the liquid storage tanks (3, 4) using the central controller (10), the volume magnitude and the rate of change of the volume for the liquid in the liquid storage tanks (3, 4) can be exactly obtained in time. The electrolyzed oxidizing water generators (2) are effectively controlled based on above data. An intelligent control method for the system is also provided.

5 Claims, 2 Drawing Sheets

(51) Int. Cl.
  *C02F 1/46* (2006.01)
  *C02F 1/66* (2006.01)
  *C02F 1/72* (2006.01)
  *C25B 1/00* (2006.01)
  *A61L 2/03* (2006.01)
  *C02F 1/467* (2006.01)
  *C02F 1/461* (2006.01)

(52) U.S. Cl.
  CPC ...... *C02F 2001/4619* (2013.01); *C02F 1/4618* (2013.01)
  USPC ............. 210/86; 204/555; 204/556; 210/104; 210/138; 210/143; 210/198.1; 210/243; 210/259; 210/263; 210/748.01

(56) References Cited

U.S. PATENT DOCUMENTS

| | | | |
|---|---|---|---|
| 7,487,677 B2* | 2/2009 | Chai et al. | 73/304 R |
| 8,419,926 B2* | 4/2013 | Miyashita et al. | 205/743 |
| 2001/0022273 A1* | 9/2001 | Popov et al. | 204/518 |
| 2002/0032141 A1 | 3/2002 | Harkins | |
| 2002/0175085 A1 | 11/2002 | Harkins et al. | |
| 2004/0256243 A1* | 12/2004 | Hara | 205/628 |
| 2008/0292537 A1* | 11/2008 | Sano | 423/580.1 |
| 2008/0302651 A1* | 12/2008 | Arai et al. | 204/157.15 |
| 2009/0071843 A1* | 3/2009 | Miyashita et al. | 205/746 |

FOREIGN PATENT DOCUMENTS

| | | |
|---|---|---|
| CN | 101526821 A | 9/2009 |
| DE | 20 2008 005 180 U1 | 7/2008 |
| JP | 7-155762 * | 7/1995 |
| JP | 2003-80252 * | 3/2003 |
| JP | 2004-97977 | 4/2004 |

OTHER PUBLICATIONS

Derwent Abstract for JP 7-155762, Jul. 1995.*
International Search Report for PCT/CN2010/071059, mailed Jul. 1, 2010.

* cited by examiner

CENTRALIZED SUPPLY SYSTEM FOR ELECTROLYZED OXIDIZING WATER AND INTELLIGENT CONTROL METHOD THEREOF

FIELD OF THE INVENTION

The invention relates to automatic control field, specifically, relates to a centralized supply system for electrolyzed oxidizing water and the intelligent control method thereof.

BACKGROUND OF THE INVENTION

The electrolyzed oxidizing water is rapidly popularized and applied in medical treatment, agriculture, animal husbandry, food processing and catering industry, and public traffic because it has features of having specifically efficient sterilisation capacity, without penetrating odor, no thrill on human organ, skin tissue, mucosa and etc., nontoxic and no side effect, resulting in no pollution on environment when discharged.

The electrolyzed oxidizing water is mainly manufactured by electrolyzed oxidizing water generators, and water yield of the electrolyzed oxidizing water generator mainly depends on performance of the core component-electrobath. Due to cost constraint, capacity of current domestic and international electrobath generally maintains at 1-4 L/min of electrolyzed oxidizing water yield, and generally water output of a tap is required at least at 3 L/min. Thus, one electrolyzed oxidizing water generator only satisfies practical demand of a single water consuming point at most.

To meet widespread requirement of electrolyzed oxidizing water in related industries, people commonly provide liquid storage tanks (canisters), ensure the electrolyzed oxidizing water generators continuously operate, store the generated electrolyzed oxidizing water in liquid storage tanks (canisters), and arrange dedicated pipe from the liquid storage tanks (canisters) to each water consuming terminal, so that water can be directly drained out from taps when the water consuming terminals need water. Although such method can solve the problem that a plurality of water consuming terminals simultaneously use electrolyzed oxidizing water in certain area, the problem of the electrolyzed oxidizing water in short supply is still possible to occur when there are relatively more water consuming points and relatively large instantaneous water consumption. For this end, people apply a plurality of electrolyzed oxidizing water generators and make them work in parallel, and enlarge volume capacity of liquid storage tanks (canisters). These methods are capable of solving the problem of the electrolyzed oxidizing water in short supply to some extent, but have some potential harmful effects.

Since its disinfection and sterilization effect has direct relation with its physicochemical index (ORP, pH value and available chlorine), the electrolyzed oxidizing water would be gradually reduced to common water when it contact light, air and organic matter during storage and would loss disinfection and sterilization effect. And it's proved through experiment: in closed environment, if the storage time of the electrolyzed oxidizing water is too long, its physicochemical index would also decreases, and its disinfection and sterilization effect would also be reduced.

When the volume capacity of the liquid storage tank (canister) is relatively large, possible fluctuation of the water consumption would probably result in the residence time of the electrolyzed oxidizing water in the liquid storage tank (canister) too long, so that the physicochemical index of the electrolyzed oxidizing water decreases and affecting its disinfection and sterilization effect. Therefore, it's always the task explored in the industry of electrolyzed oxidizing water to not only satisfy timely use in water consuming point, but also guarantee the residence time of electrolyzed oxidizing water in the liquid storage tank (canister) as short as possible so as to ensure its excellent disinfection and sterilization effect.

Meanwhile, since the centralized supply system for electrolyzed oxidizing water that applies a plurality of electrolyzed oxidizing water generators working in parallel has a relatively large scale, generally an independent equipment room is needed, thus operation and maintenance, and monitoring and management of devices is a key point in the whole system management. If unattended operation and remote monitoring can be realized, undoubtedly workload of attendant can be reduced, and automatization level of system and user's information system management level can be improved.

SUMMARY OF THE INVENTION

With respect to the prior art and existed problems, the invention proposes a centralized supply system for electrolyzed oxidizing water and the intelligent control method thereof, aiming to solve the problem of requiring abundant electrolyzed oxidizing water to perform disinfection and sterilization in the fields of medical treatment, agriculture, food, traffic and public health, and etc. With a plurality of electrolyzed oxidizing water generators connected in parallel applied, the invention use an intelligent control method to perform centralized and unified management and optimal operation on the whole system through a central controller, which not only satisfies timely use in water consuming point, but also makes residence time of newly manufactured electrolyzed oxidizing water in the liquid storage tank as short as possible, so as to keep excellent disinfection and sterilization effect of the electrolyzed oxidizing water. Meanwhile, by arranging communication cables between the system device and user-related device management mechanism, the computer of management mechanism is connected with the central controller in equipment room through cables, so that operation of system device can be monitored and controlled in real time through remote computer of device management mechanism, and long-time storage and inquiry of device operation, physicochemical index of output water, historical data, alarm state and etc, can be realized, so as to conveniently monitor and manage the electrolyzed oxidizing water system.

The centralized supply system for electrolyzed oxidizing water of the invention comprises a water softener, an electrolyzer delivery device, a plurality of electrolyzed oxidizing water generators connected in parallel, liquid storage tanks and delivery pumps, characterized in that: providing an independent central controller, which is connected with each of the plurality of electrolyzed oxidizing water generators connected in parallel respectively through communication cables, and controls start and stop of each electrolyzed oxidizing water generator by sending controlling signal through communication cable; providing liquid level sensors in the liquid storage tanks, which send liquid level signals in the liquid storage tanks to the central controller; the central controller calculating the liquid volume in the liquid storage tanks based on the liquid level signals, and determines the change rate of the liquid volume in the liquid storage tank by calculating the liquid volume in the liquid storage tank in timing mode, so as to determine to start one, two, a plurality of or all electrolyzed oxidizing water generators.

The central controller is connected to a computer located in monitoring center through communication cable, and administrator monitors the operation of the plurality of electrolyzed oxidizing water generators connected in parallel remotely through computer.

The central controller determines three water levels according to the liquid volume: low water level, general water level and standard water level, and determines three levels of change rate of the liquid volume: fast change, slow change and generally no change.

The invention also provides an intelligent control method for centralized supply system for electrolyzed oxidizing water, the system comprising a water softener, a plurality of electrolyzed oxidizing water generators connected in parallel, liquid storage tanks and delivery pumps, which is characterized in that: a central controller is arranged and performs independent control to each of the electrolyzed oxidizing water generators connected in parallel, liquid level sensors are arranged in the liquid storage tanks and are connected with the central controller through data collection cables, the steps of the control method performed by the central controller are:

(1) at regular interval $\Delta_T$, the central controller calculates the liquid volume V in the liquid storage tank based on signal of the liquid level sensor, simultaneously calculates the change quantity $\Delta V_1$ of the liquid volume in the liquid storage tank and the change rate $\Delta V$ of the liquid volume in the liquid storage tank during $\Delta_T$, wherein $\Delta V = \Delta V_1 / \Delta_T$;

(2) the water level in the liquid storage tank is divided into three levels: low water level, general water level and standard water level, and corresponding liquid volume is represented with $V_{low}$, $V_{com.}$ and $V_{std.}$ respectively with the relationships being $V_{low} < V_{com.} < V_{std.}$, and the change rate of the liquid volume in the liquid storage tank is divided into fast change, slow change and generally no change and corresponding change rate of the liquid volume in the liquid storage tank is represented with $\Delta_{fast}$, $\Delta_{slow}$ and $\Delta_{none}$ with the relationships being $\Delta_{fast} > \Delta_{slow} > \Delta_{none}$;

(3) the central controller performs control to the plurality of electrolyzed oxidizing water generators connected in parallel in accordance with the following situations:

(3.1) when $V \leq V_{low}$, $\Delta V < 0$, $|\Delta V| \geq \Delta_{slow}$, that explains the water consumption is relatively large, and the instantaneous water consumption is also relatively large, and all electrolyzed oxidizing water generators should be started to manufacture water for supplement;

(3.2) when $V \leq V_{low}$, $\Delta V < 0$, $|\Delta V| \geq \Delta_{none}$, that explains the instantaneous water consumption gradually reduces, thus a small part of electrolyzed oxidizing water generators can be stopped and only a large part of electrolyzed oxidizing water generators should be started to manufacture water;

(3.3) when $V \leq V_{low}$, $\Delta V \geq \Delta_{fast}$, that explains the water manufacture amount is larger than the instantaneous water consumption amount, water quantity in the liquid storage tank increases quickly, thus only a part of electrolyzed oxidizing water generators should be started to manufacture water;

(3.4) when $V \leq V_{com.}$, $\Delta V < 0$, $|\Delta V| \geq \Delta_{fast}$, that explains the instantaneous water consumption is relatively large, water quantity in the liquid storage tank decreases quickly, thus more electrolyzed oxidizing water generators should be started to manufacture water;

(3.5) when $V \leq V_{com.}$, $\Delta V < 0$, $|\Delta V| \geq \Delta_{none}$, that explains the instantaneous water consumption gradually decreases, thus number of the electrolyzed oxidizing water generators to be started can be reduced;

(3.6) when $V \leq V_{com.}$, $\Delta V \geq \Delta_{fast}$, that explains water quantity in the liquid storage tank continuously increases, thus only a small part of or a single electrolyzed oxidizing water generator should be started to manufacture water;

(3.7) when $V \leq V_{com.}$, $\Delta V \geq V_{none}$, that explains the instantaneous water consumption gradually decreases, water quantity in the liquid storage tank slowly increases, thus only a small part of or a single electrolyzed oxidizing water generator should be started to manufacture water;

(3.8) when $V \geq V_{std.}$, all electrolyzed oxidizing water generators should be stopped;

(3.9) when $V > V_{com.}$, $\Delta V < 0$, $|\Delta V| \geq \Delta_{fast}$, that explains the instantaneous water consumption increases, thus a small part of or a single electrolyzed oxidizing water generator should be started to manufacture water;

(3.10) when $V > V_{com.}$, $\Delta V \geq \Delta_{none}$, that explains water quantity in the liquid storage tank slowly increases, and all electrolyzed oxidizing water generators should be stopped; and (4) the central controller starts/stops each of the plurality of electrolyzed oxidizing water generators through performing mechanism in accordance with the above controlling signals.

In the technical solution of the invention, an independent central controller is provided, which is connected with each of the plurality of electrolyzed oxidizing water generators connected in parallel respectively through communication cables, and controls start and stop of each electrolyzed oxidizing water generator by sending controlling signal through communication cable.

Liquid level sensors are provided in the liquid storage tanks, which send liquid level signals in the liquid storage tanks to the central controller, and the central controller calculates the liquid volume in the liquid storage tanks based on the liquid level signals, and determines three water levels according to the liquid volume: low water level, general water level and standard water level. The central controller calculates the liquid volume in the liquid storage tanks in timing mode, so as to determine the change rate of the liquid volume in the liquid storage tank, and determines three levels of change rate of the liquid volume: fast change, slow change and generally no change.

In accordance with three water levels of the liquid volume: low water level, general water level and standard water level, and three levels of change rate of the liquid volume: fast change, slow change and generally no change, the central controller determines to start one, two, a plurality of or all electrolyzed oxidizing water generators.

By arranging communication cable between the central controller and computer of user-related device management mechanism and programming relevant software, the device management mechanism could realize remote monitoring management of the central controller and various electrolyzed oxidizing water generators.

Main advantages of the intelligent control method of the invention are:

Through detection, judgment and calculation of the central controller to the liquid level signals in the liquid storage tank, liquid volume and change rate of the liquid volume in the liquid storage tank can be accurately known in time, so that the electrolyzed oxidizing water generators can be effectively controlled, which not only ensure use in each water consuming point, but also guarantee the residence time of the electrolyzed oxidizing water in the liquid storage tank as short as possible, so as to keep the excellent disinfection and sterilization effect of the electrolyzed oxidizing water.

Meanwhile, through communication between the central controller and control management center, remote monitoring of the electrolyzed oxidizing water system by the control management center could be realized, and unattended opera-

DESCRIPTION OF REFERENCE NUMBER

1—water softener, 2—a plurality of electrolyzed oxidizing water generators connected in parallel, 3—alkaline water storage tank, 4—acid water storage tank, 5—alkaline water delivery pump, 6—acid water delivery pump, 7—alkaline water delivery pipe, 8—acid water delivery pipe, 9—liquid level sensor, 10—central controller, 11—communication cable between the central controller with the electrolyzed oxidizing water generator, 12—communication cable between the central controller and the liquid level sensor, 13—computer in monitoring center, 14—communication cable between the central controller and the computer in monitoring center, 16—electrolyzer delivery device, 17—communication cable between the central controller and the electrolyzer delivery device.

DETAILED DESCRIPTION OF THE INVENTION

Figure 1:
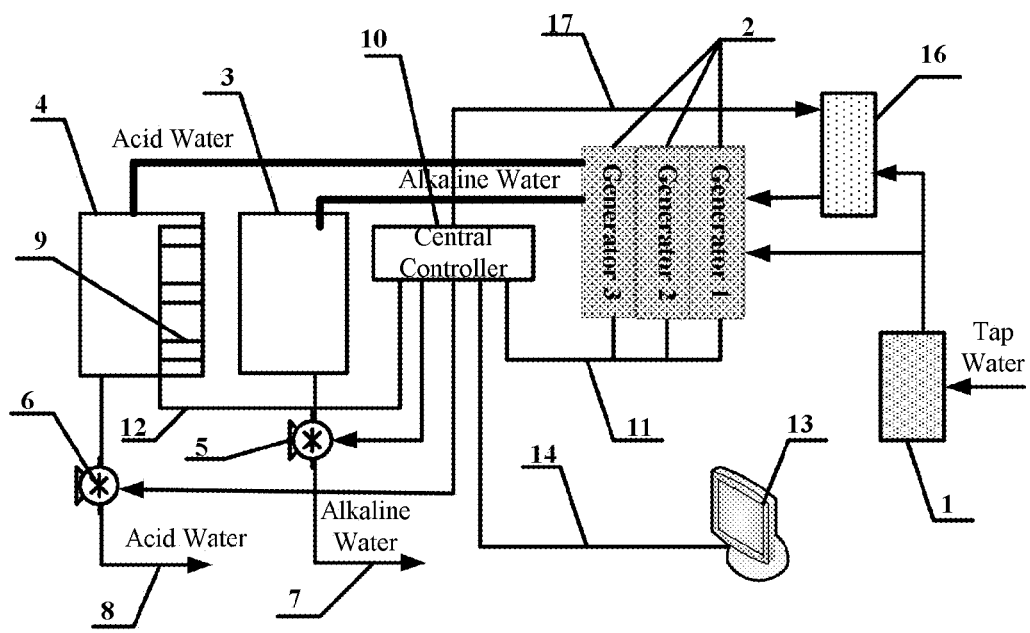
FIG. 1 is a layout structure view of the centralized supply system for electrolyzed oxidizing water according to an embodiment of the invention.

Detailed description of one embodiment of the invention will be further made in conjunction with appended drawings:

As shown in FIG. 1, the centralized supply system for electrolyzed oxidizing water comprises: a water softener 1 connected to water source; an electrolyzer delivery device 16 connected with the water softener 1 through a pipe; 3 electrolyzed oxidizing water generators 2 connected in parallel that are connected with the electrolyzer delivery device 16 through pipes; an alkaline water storage tank 3 and an acid water storage tank 4 that are connected with the 3 electrolyzed oxidizing water generators 2 connected in parallel through pipes; an alkaline water delivery pump 5 connected with the alkaline water storage tank 3 through a pipe and an acid water delivery pump 6 connected with the acid water storage tank 4 through a pipe; characterized in that: the system further comprises a central controller 10, which is connected with the 3 electrolyzed oxidizing water generators 2 connected in parallel respectively through communication cables, performs independent control to each of the 3 electrolyzed oxidizing water generators 2 connected in parallel, and controls start and stop of each electrolyzed oxidizing water generator 2 by sending controlling signal through communication cable; liquid level sensors 9 which are respectively installed in the alkaline water storage tank 3 and acid water storage tank 4, connected to the central controller 10 through communication cable 12 and sending liquid level signals to the central controller 10; the central controller 10 calculates the liquid volume in the liquid storage tanks based on liquid level signals, and determines the change rate of the liquid volume in the liquid storage tanks by calculating the liquid volume in the liquid storage tank in timing mode, so as to determine to start one, two, a plurality of or all electrolyzed oxidizing water generators 2, simultaneously sends instruction to the electrolyzer delivery device 16 through communication cable, requiring the electrolyzer delivery device 16 to deliver electrolyzer.

Moreover, the central controller 10 is connected to a computer 13 located in monitoring center through communication cable, and administrator monitors the operation of the 3 electrolyzed oxidizing water generators 2 remotely through computer 13.

In accordance with an example of the invention, the central controller 10 determines three water levels according to the liquid volume: low water level, general water level and standard water level, and determines three levels of change rate of the liquid volume: fast change, slow change and generally no change. Those skilled in the art also can determine different criterions in terms of practical situation.

In an example of the invention, there are 9 floors of wards in a hospital, and totally 50 water consuming points of electrolyzed oxidizing water. Manufacture and supply center of the electrolyzed oxidizing water is provided in a dedicated computer room on the top floor, for use of 3 electrolyzed oxidizing water generators 2 working in parallel. The central controller 10 is connected to a computer 13 in devices room through communication cable, and administrator can monitor operation of the 3 electrolyzed oxidizing water generators 2 in the manufacture and supply center of through the computer 13.

The centralized supply system for electrolyzed oxidizing water comprises a water softener 1, an electrolyzer delivery device 16, 3 electrolyzed oxidizing water generators 2 connected in parallel, an alkaline water storage tank 3 and an acid water storage tank 4, an alkaline water delivery pump 5 and an acid water delivery pump 6, characterized in that: a central controller 10 is arranged and performs independent control to each of the 3 electrolyzed oxidizing water generators 2 connected in parallel, liquid level sensors 9 are arranged in the liquid storage tank 3 and/or 4 and are connected with the central controller 10 through a data collection cable 12, steps of the control method performed by the central controller 10 with the technical solution of the invention are (referring to the flow chart of FIG. 2):

(1) At regular interval $\Delta T$, the central controller 10 calculates the liquid volume V in the liquid storage tank 3 or 4 based on signals of the liquid level sensors 9, simultaneously calculates the change quantity $\Delta V_1$ of the liquid volume in the liquid storage tank 3 or 4 and the change rate $\Delta V$ of the liquid volume in the liquid storage tank 3 or 4 in $\Delta_T$, wherein $\Delta V = \Delta V_1 / \Delta_T$;

(2) The water level in the liquid storage tank 3 or 4 is divided into three levels: low water level, general water level and standard water level, and corresponding liquid volume is represented with $V_{low}$, $V_{com.}$ and $V_{std.}$ respectively with the relationships being $V_{low} < V_{com.} < V_{std.}$, and the change rate of the liquid volume in the liquid storage tank 3 or 4 is divided into fast change, slow change and generally no change and corresponding change rate of the liquid volume in the liquid storage tank 3 or 4 is represented with $\Delta_{fast}$, $\Delta_{slow}$ and $\Delta_{none}$ with the relationships being $\Delta_{fast} > \Delta_{slow} > \Delta_{none}$;

In the example, volume capacity of the liquid storage tank 3 or 4 is 1000 L, output quantity of the electrolyzed oxidizing water in water consuming point is 3 L/min, 50 water consuming points are assumed to used simultaneously based on probability of 40%, 25% and 10%, and the total water outputting speed is respectively 60 L/min, 36 L/min and 15 L/min. Generally, in a water consuming point, once water consumption is assumed as 10 L (continuously draining water for 3 minutes), the calculated total water consumption based on the above probability is respectively 180 L, 108 L and 45 L. Thus values of $V_{low}$, $V_{com.}$ and $V_{std.}$ are respectively supposed as 200 L, 400 L and 600 L, and values of $\Delta_{fast}$, $\Delta_{slow}$ and $\Delta_{none}$ are respectively supposed as 50 L/min, 30 L/min and 10 L/min.

(3) The central controller 10 performs control to 3 electrolyzed oxidizing water generators 2 connected in parallel in accordance with the following situations:

(3.1) when $V \leq V_{low}$, $\Delta V<0$, $|\Delta V| \geq \Delta_{slow}$, that explains the water consumption is relatively large, and the instantaneous water consumption is also relatively large, and all electrolyzed oxidizing water generators 2 should be started to manufacture water for supplement;

(3.2) when $V \leq V_{low}$, $\Delta V<0$, $|\Delta V| \geq \Delta_{none}$, that explains the instantaneous water consumption gradually reduces, thus a small part of electrolyzed oxidizing water generators 2 can be stopped and only a large part of electrolyzed oxidizing water generators 2 should be started to manufacture water;

(3.3) when $V \leq V_{low}$, $\Delta V \geq \Delta_{fast}$, that explains the water manufacture amount is larger than the instantaneous water consumption, water quantity in the liquid storage tank 3 or 4 increases quickly, thus only part electrolyzed oxidizing water generators 2 should be started to manufacture water;

(3.4) when $V \leq V_{com.}$, $\Delta V<0$, $|\Delta V| \geq \Delta_{fast}$, that explains the instantaneous water consumption is relatively large, water quantity in the liquid storage tank 3 or 4 decreases quickly, thus more electrolyzed oxidizing water generators 2 should be started to manufacture water;

(3.5) when $V \leq V_{com.}$, $\Delta V<0$, $|\Delta V| \geq \Delta_{none}$, that explains the instantaneous water consumption gradually decreases, thus number of the electrolyzed oxidizing water generators 2 to be started can be reduced;

(3.6) when $V \leq V_{com.}$, $\Delta V \geq \Delta_{fast}$, that explains water quantity in the liquid storage tank 3 or 4 continuously increases, thus only a small part of or a single electrolyzed oxidizing water generator 2 should be started to manufacture water;

(3.7) when $V \leq V_{com.}$, $\Delta V \geq \Delta_{none}$, that explains the instantaneous water consumption gradually decreases, water quantity in the liquid storage tank 3 or 4 slowly increases, thus only a small part of or a single electrolyzed oxidizing water generator 2 should be started to manufacture water;

(3.8) when $V \geq V_{std.}$, all electrolyzed oxidizing water generators 2 should be stopped;

(3.9) when $V > V_{com.}$, $\Delta V<0$, $|\Delta V| \geq \Delta_{fast}$, that explains the instantaneous water consumption increases, thus a small part of or a single electrolyzed oxidizing water generator 2 should be started to manufacture water;

(3.10) when $V > V_{com.}$, $\Delta V \geq \Delta_{none}$, that explains water quantity in the liquid storage tank 3 or 4 slowly increases, and all electrolyzed oxidizing water generators 2 should be stopped; and (4) The central controller 10 starts/stops each electrolyzed oxidizing water generator 2 through performing mechanism in accordance with the above controlling signals.

Figure 2:
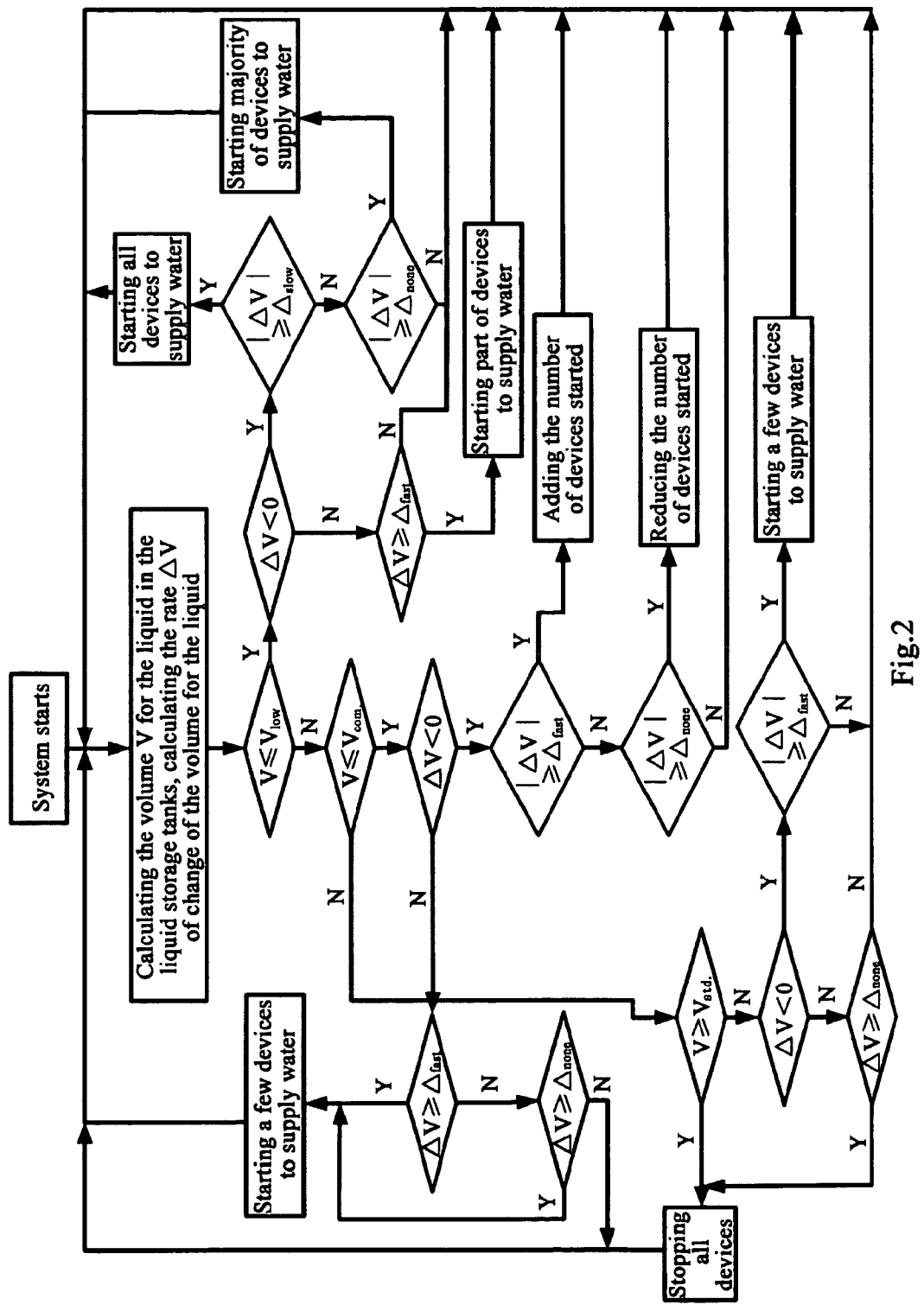
FIG. 2 is a control flow chart of the intelligent control method for centralized supply system for electrolyzed oxidizing water according to an embodiment of the invention.

As shown in FIG. 2, by monitoring the position signals of liquid level sensors 9 in timing mode, the central controller 10 performs dispatch on the 3 electrolyzed oxidizing water generators 2. As an example, the practical dispatching method in the above controlling process is as follows:

The central controller 10 calculates the liquid volume V in the liquid storage tank 3 or 4 in accordance with the signals of the liquid level sensors 9 every 2 minutes, and if the calculated value of V is 200, $\Delta V$ is −40, the central controller would automatically start all 3 electrolyzed oxidizing water generators 2 to manufacture water;

If the calculated value of V is 150, $\Delta V$ is 60, only 2 electrolyzed oxidizing water generators 2 are started;

If the calculated value of V is 400, $\Delta V$ is −80, the number of electrolyzed oxidizing water generators 2 is to be increased;

If the calculated value of V is 300, $\Delta V$ is −20, the number of electrolyzed oxidizing water generators 2 is to be decreased;

If the calculated value of V is 350, $\Delta V$ is 20, only 1 electrolyzed oxidizing water generator 2 is started;

If the calculated value of V is 250, $\Delta V$ is 60, only 1 electrolyzed oxidizing water generator 2 is started;

If the calculated value of V is 650, all electrolyzed oxidizing water generators 2 are stopped;

If the calculated value of V is 450, $\Delta V$ is −60, only 1 electrolyzed oxidizing water generators 2 is started; and If the calculated value of V is 600, $\Delta V$ is 20, all electrolyzed oxidizing water generators 2 are stopped.

The above process is realized by programming control, and the control program is stored in the central controller 10, and according to instruction of computer 13 in monitoring center, determines start/stop of various electrolyzed oxidizing water generators 2, open/close of the delivery pumps 5 and 6, or delivery of situation of various electrolyzed oxidizing water generators 2, physicochemical index of output water and breakdown information. The computer 13 in monitoring center stores and classifies the information from the central controller 10, for longtime storage and inquiry.

The above example shows that the central controller 10 performs dispatch on the 3 electrolyzed oxidizing water generators 2 by monitoring the position signals of the liquid level sensors 9 in timing mode, which ensures the liquid volume in the liquid storage tank 3 or 4 not more than 650 L, and not less than 150 L. Such method not only ensure normal use in water consuming point, but also guarantee the residence time of newly manufactured electrolyzed water in the liquid storage tank 3 or 4 as short as possible, so as to keep excellent disinfection and sterilization effect of electrolyzed oxidizing water.

The above example mainly explains the system and its control method of the invention. Although descriptions are made on some embodiments of the invention, those skilled in the art should understand the invention can be performed in many other forms which do not depart from its spirit and scopes, for example, those skilled in the art can determine different criterions for liquid volume and change rate of liquid volume according to practical situation, such as applying more levels for more accurate control. Therefore, the exemplary embodiment is for schematic illustration but not restrictive, and various modifications and variations are possibly included in the invention if only they don't depart from the spirit and scope defined by the Claims appended hereto.

What is claimed is:

1. A centralized supply system for electrolyzed oxidizing water, comprising:
   a water softener connected to a water source;
   an electrolyzer delivery device connected with the water softener through a pipe;
   a plurality of electrolyzed oxidizing water generators connected in parallel that are connected with the electrolyzer delivery device through pipes;
   an alkaline water storage tank and an acid water storage tank that are connected with the plurality of electrolyzed oxidizing water generators connected in parallel through pipes;
   an alkaline water delivery pump connected with the alkaline water storage tank through a pipe and an acid water delivery pump connected with the acid water storage tank through a pipe;

a central controller, which is connected with the plurality of electrolyzed oxidizing water generators connected in parallel, performs independent control over each of the plurality of electrolyzed oxidizing water generators connected in parallel, and controls starting and stopping of each of the plurality of electrolyzed oxidizing water generators connected in parallel by sending a controlling signal; and liquid level sensors which are respectively installed in the alkaline water storage tank and acid water storage tank, connected to the central controller, and send respective liquid level signals to the central controller;

wherein the central controller calculates a liquid volume in one of the alkaline water storage tank and the acid water storage tank based on the respective liquid level signal, and determines a change rate of the liquid volume in the one of the alkaline water storage tank and the acid water storage tank by calculating the liquid volume in the one of the alkaline water storage tank and the acid water storage tank at a regular interval, so as to determine whether to start one, two, a plurality of, or all of the electrolyzed oxidizing water generators and simultaneously send instruction to the electrolyzer delivery device, requiring the electrolyzer delivery device to deliver electrolyzer.

2. The centralized supply system for electrolyzed oxidizing water according to claim 1, wherein the central controller is connected to a computer located in a monitoring center to permit monitoring of the plurality of electrolyzed oxidizing water generators connected in parallel remotely through the computer.

3. The centralized supply system for electrolyzed oxidizing water according to claim 2, wherein:

1) at the regular interval $\Delta_T$, the central controller calculates the liquid volume V in the one of the alkaline water storage tank and the acid water storage tank based on signal of the liquid level sensor, simultaneously calculates the change quantity $\Delta V_1$ of the liquid volume in the one of the alkaline water storage tank and the acid water storage tank and the change rate $\Delta V$ of the liquid volume in the one of the alkaline water storage tank and the acid water storage tank during $\Delta_T$, wherein $\Delta V = \Delta V_1/\Delta_T$;

2) the water level in the one of the alkaline water storage tank and the acid water storage tank is divided into three levels: low water level, general water level and standard water level, and corresponding liquid volume is represented with $V_{low}$, $V_{com.}$ and $V_{std.}$ respectively with the relationships being $V_{low} < V_{com.} < V_{std.}$, and the change rate of the liquid volume in the one of the alkaline water storage tank and the acid water storage tank is divided into fast change, slow change and generally no change, and a corresponding change rate of the liquid volume in the one of the alkaline water storage tank and the acid water storage tank is represented with $\Delta_{fast}$, $\Delta_{slow}$ and $\Delta_{none}$ with the relationships being $\Delta_{fast} > \Delta_{slow} > \Delta_{none}$;

3) the central controller performs control over the plurality of electrolyzed oxidizing water generators connected in parallel in accordance with the following situations:

3.1) when $V \leq V_{low}$, $\Delta V < 0$, $|\Delta V| \geq \Delta_{slow}$, controller causes all of the plurality of electrolyzed oxidizing water generators to be started to manufacture water for supplement;

3.2) when $V \leq V_{low}$, $\Delta V < 0$, $|\Delta V| \geq \Delta_{none}$, which indicates that instantaneous water consumption gradually reduces, the controller causes only a portion of the plurality of electrolyzed oxidizing water generators to be started to manufacture water;

3.3) when $V \leq V_{low}$, $\Delta V \geq \Delta_{fast}$, which indicates that a water manufacture amount is larger than an instantaneous water consumption amount, and water quantity in the one of the alkaline water storage tank and the acid water storage tank increases quickly, the controller causes only a portion of the plurality of electrolyzed oxidizing water generators, smaller than the portion to be started when $V \leq V_{low}$, $\Delta V < 0$, $|\Delta V| \geq \Delta_{none}$, to be started to manufacture water;

3.4) when $V \leq V_{com.}$, $\Delta V < 0$, $|\Delta V| \geq \Delta_{fast}$, the controller causes more of the plurality of electrolyzed oxidizing water generators to be started to manufacture water;

3.5) when $V \leq V_{com.}$, $\Delta V < 0$, $|\Delta V| \geq \Delta_{none}$, which indicates that instantaneous water consumption gradually decreases, the controller causes a quantity of the plurality of electrolyzed oxidizing water generators manufacturing water to be reduced;

3.6) when $V \leq V_{com.}$, $\Delta V \geq \Delta_{fast}$, which indicates that water quantity in the one of the alkaline water storage tank and the acid water storage tank continuously increases, the controller causes only a single one of the plurality of electrolyzed oxidizing water generators or a small portion thereof, smaller than the portion to be started when $V \leq V_{low}$, $\Delta V \geq \Delta_{fast}$, to be started to manufacture water;

3.7) when $V \leq V_{com.}$, $\Delta V \geq \Delta_{none}$, which indicates that instantaneous water consumption gradually decreases, water quantity in the one of the alkaline water storage tank and the acid water storage tank slowly increases, the controller causes only a single one of the plurality of electrolyzed oxidizing water generator or a portion thereof, smaller than the portion to be started when $V \leq V_{low}$, $\Delta V \geq \Delta_{fast}$, to be started to manufacture water;

3.8) when $V \geq V_{std.}$, the controller causes all of the plurality of electrolyzed oxidizing water generators to be stopped;

3.9) when $V > V_{com.}$, $\Delta V < 0$, $|\Delta V| \geq \Delta_{fast}$, which indicates that instantaneous water consumption increases, the controller causes only a single one of the plurality of electrolyzed oxidizing water generators or a portion thereof, smaller than the portion to be started when $V \leq V_{low}$, $\Delta V \geq \Delta_{fast}$, to be started to manufacture water; and 3.10) when $V > V_{com.}$, $\Delta V \geq \Delta_{none}$, which indicates that water quantity in the one of the alkaline water storage tank and the acid water storage tank slowly increases, the controller causes all of the electrolyzed oxidizing water generators to be stopped.

4. The centralized supply system for electrolyzed oxidizing water according to claim 1, wherein:

1) at the regular interval $\Delta_T$, the central controller calculates the liquid volume V in the one of the alkaline water storage tank and the acid water storage tank based on a signal of the liquid level sensor, and simultaneously calculates the change quantity $\Delta V_1$ of the liquid volume in the one of the alkaline water storage tank and the acid water storage tank and the change rate $\Delta V$ of the liquid volume in the one of the alkaline water storage tank and the acid water storage tank during $\Delta_T$, wherein $\Delta V = \Delta V_1/\Delta_T$;

2) water level in the one of the alkaline water storage tank and the acid water storage tank is divided into three levels: low water level, general water level and standard water level, a corresponding liquid volume is represented with $V_{low}$, $V_{com.}$ and $V_{std.}$ respectively with the relationships being $V_{low} < V_{com.} < V_{std.}$, the change rate of the liquid volume in the one of the alkaline water storage tank and the acid water storage tank is divided into fast change, slow change, and generally no change, and a corresponding change rate of the liquid volume in the one of the alkaline water storage tank and the acid water storage tank is represented with $\Delta_{fast}$, $\Delta_{slow}$ and $\Delta_{none}$ with the relationships being $\Delta_{fast} > \Delta_{slow} > \Delta_{none}$; and 3) the central controller performs control over the plurality of electrolyzed oxidizing water generators connected in parallel in accordance with the following situations:

3.1) when $V \leq V_{low}$, $\Delta V < 0$, $|\Delta V| \geq \Delta_{slow}$, the controller causes all of the plurality of electrolyzed oxidizing water generators to be started to manufacture water for supplement;

3.2) when $V \leq V_{low}$, $\Delta V < 0$, $|\Delta V| \geq \Delta_{none}$, which indicates that instantaneous water consumption gradually reduces, the controller causes only a portion of the plurality of electrolyzed oxidizing water generators to be started to manufacture water;

3.3) when $V \leq V_{low}$, $\Delta V \geq \Delta_{fast}$, which indicates that a water manufacture amount is larger than an instantaneous water consumption amount, and water quantity in the one of the alkaline water storage tank and the acid water storage tank increases quickly, the controller causes only a portion of the plurality of electrolyzed oxidizing water generators, smaller than the portion to be started when $V \leq V_{low}$, $\Delta V < 0$, $|\Delta V| \geq \Delta_{none}$, to be started to manufacture water;

3.4) when $V \leq V_{com.}$, $\Delta V < 0$, $|\Delta V| \geq \Delta_{fast}$, the controller causes more of the plurality of electrolyzed oxidizing water generators to be started to manufacture water;

3.5) when $V \leq V_{com.}$, $\Delta V < 0$, $|\Delta V| \geq \Delta_{none}$, which indicates that instantaneous water consumption gradually decreases, the controller causes quantity of the plurality of electrolyzed oxidizing water generators manufacturing water to be reduced;

3.6) when $V \leq V_{com.}$, $\Delta V \geq \Delta_{fast}$, which indicates that water quantity in the one of the alkaline water storage tank and the acid water storage tank continuously increases, the controller causes only a single one of the plurality of electrolyzed oxidizing water generators or a small portion thereof, smaller than the portion to be started when $V \leq V_{low}$, $\Delta V \geq \Delta_{fast}$, to be started to manufacture water;

3.7) when $V \leq V_{com.}$, $\Delta V \geq \Delta_{none}$, which indicates that instantaneous water consumption gradually decreases, water quantity in the one of the alkaline water storage tank and the acid water storage tank slowly increases, the controller causes only a single one of the plurality of electrolyzed oxidizing water generator or a portion thereof, smaller than the portion to be started when $V \leq V_{low}$, $\Delta V \geq \Delta_{fast}$, to be started to manufacture water;

3.8) when $V \geq V_{std.}$, the controller causes all of the plurality of electrolyzed oxidizing water generators to be stopped;

3.9) when $V > V_{com.}$, $\Delta V < 0$, $|\Delta V| \geq \Delta_{fast}$, which indicates that instantaneous water consumption increases, the controller causes only a single one of the plurality of electrolyzed oxidizing water generators or a portion thereof, smaller than the portion to be started when $V \leq V_{low}$, $\Delta V \geq \Delta_{fast}$, to be started to manufacture water; and 3.10) when $V > V_{com.}$, $\Delta V \geq \Delta_{none}$, which indicates that water quantity in the one of the alkaline water storage tank and the acid water storage tank slowly increases, the controller causes all of the electrolyzed oxidizing water generators to be stopped.

5. An intelligent control method for centralized supply system for electrolyzed oxidizing water, the system comprising:

a water softener;

a plurality of electrolyzed oxidizing water generators connected in parallel;

liquid storage tanks and delivery pumps;

a central controller that performs independent control over each of the plurality of electrolyzed oxidizing water generators connected in parallel; and liquid level sensors arranged in the liquid storage tanks and connected with the central controller through data acquisition cables, wherein:

1) at the regular interval, $\Delta_T$, the central controller calculates a liquid volume V in a liquid storage tank, being one of the liquid storage tanks, based on signals of the liquid level sensors, and simultaneously calculates the change quantity $\Delta V_1$ of the liquid volume in the liquid storage tank and the change rate $\Delta V$ of the liquid volume in the liquid storage tank in $\Delta_T$, wherein $\Delta V = \Delta V_1 / \Delta_T$;

2) water level in the liquid storage tank is divided into three levels: low water level, general water level and standard water level, and a corresponding liquid volume is represented with $V_{low}$, $V_{com.}$ and $V_{std.}$ respectively with the relationships being $V_{low} < V_{com.} < V_{std.}$, and the change rate of the liquid volume in the liquid storage tank is divided into fast variance, slow variance and generally no change, and a corresponding change rate of the liquid volume in the liquid storage tank is represented with $\Delta_{fast}$, $\Delta_{slow}$ and $\Delta_{none}$ with the relationships being $\Delta_{fast} > \Delta_{slow} > \Delta_{none}$; and 3) the central controller performs control over each of the plurality of electrolyzed oxidizing water generators connected in parallel in accordance with the following situations:

3.1) when $V \leq V_{low}$, $\Delta V < 0$, $|\Delta V| \geq \Delta_{slow}$, the controller causes all of the plurality of electrolyzed oxidizing water generators to be started to manufacture water for supplement;

3.2) when $V \leq V_{low}$, $\Delta V < 0$, $|\Delta V| \Delta_{none}$, which indicates that instantaneous water consumption gradually reduces, the controller causes only a portion of the plurality of electrolyzed oxidizing water generators to be started to manufacture water;

3.3) when $V \leq V_{low}$, $\Delta V \geq \Delta_{fast}$, swhich indicates that a water manufacture amount is larger than an instantaneous water consumption amount, water quantity in the liquid storage tank increases quickly, the controller causes only a portion of the plurality of electrolyzed oxidizing water generators, smaller than the portion to be started when $V \leq V_{low}$, $\Delta V < 0$, $|\Delta V| \geq \Delta_{none}$, to be started to manufacture water;

3.4) when $V \leq V_{com.}$, $\Delta V < 0$, $|\Delta V| \geq \Delta_{fast}$, the controller causes more of the plurality of electrolyzed oxidizing water generators to be started to manufacture water;

3.5) when $V \leq V_{com.}$, $\Delta V < 0$, $|\Delta V| \leq \Delta_{none}$, which indicates that instantaneous water consumption gradually decreases, the controller causes a quantity of the plurality of electrolyzed oxidizing water generators manufacturing water to be reduced;

3.6) when $V \leq V_{com.}$, $\Delta V \geq \Delta_{fast}$, which indicates that water quantity in the liquid storage tank continuously increases, the controller causes only a part of or a single one of the plurality of electrolyzed oxidizing water generator to be started to manufacture water;

3.7) when $V \leq V_{com.}$, $\Delta V \geq \Delta_{none}$, which indicates that instantaneous water consumption gradually decreases, water quantity in the liquid storage tank slowly increases, the controller causes only a single one of the plurality of electrolyzed oxidizing water generators or a portion thereof, smaller than the portion to be started when $V \leq V_{low}$, $\Delta V \geq \Delta_{fast}$, to be started to manufacture water;

3.8) when $V \geq V_{std.}$, the controller causes all of the plurality of electrolyzed oxidizing water generators to be stopped;

3.9) when $V > V_{com.}$, $\Delta V < 0$, $|\Delta V| \geq \Delta_{fast}$, which indicates that instantaneous water consumption increases, the controller causes only a single one of the plurality of electrolyzed oxidizing water generators or a portion thereof, smaller than the portion to be started when $V \leq V_{low}$, $\Delta V \geq \Delta_{fast}$, to be started to manufacture water; and 3.10) when $V > V_{com.}$, $\Delta V \geq \Delta_{none}$, which indicates that water quantity in the liquid storage tank slowly increases, the controller causes all of the plurality of electrolyzed oxidizing water generators to be stopped.

* * * * *

UNITED STATES PATENT AND TRADEMARK OFFICE
CERTIFICATE OF CORRECTION

| | | |
|---|---|---|
| PATENT NO. | : 8,888,997 B2 | Page 1 of 1 |
| APPLICATION NO. | : 13/239904 | |
| DATED | : November 18, 2014 | |
| INVENTOR(S) | : Dunjie Zhang et al. | |

It is certified that error appears in the above-identified patent and that said Letters Patent is hereby corrected as shown below:

On the Title Page

Add -- Item [63] (Related U.S. Application Data), Continuation of application No. PCT/CN2010/071059, filed March 18, 2010 --.

In the Specification

Column 1, Approx. Line 6, Add -- Cross Reference to Related Applications
this application is a continuation application filed under 35 U.S.C. §111(a), claiming the benefit under 35 U.S.C. §120 and §365(c) of a PCT International Application Number PCT/CN2010/071059, filed March 18, 2010, it being further noted that foreign benefit is based upon Chinese Patent Application No. 200910119759.0, filed March 26, 2009 in the State Intellectual Property Office of P.R. China, the disclosures of which are hereby incorporated by reference. --.

In the Claims

Column 10, line 64, In Claim 4, delete "$V_{com.}$," and insert -- $V_{com.}$ --, therefor.

Column 11, line 32, In Claim 4, after "causes" insert -- a --, therefor.

Column 12, line 37, In Claim 5, delete "$|\Delta V|\Delta_{none}$," and insert -- $|\Delta V| \geq \Delta_{none}$, --, therefor.

Column 12, line 42, In Claim 5, delete "swhich" and insert -- which --, therefor.

Signed and Sealed this
Fifth Day of May, 2015

Michelle K. Lee
*Director of the United States Patent and Trademark Office*